United States Patent [19]

Dimakos et al.

[11] Patent Number: 4,476,861
[45] Date of Patent: Oct. 16, 1984

[54] INSTRUMENT FOR REMOVAL OF A BONE CEMENT TUBE IN AN ARTIFICIAL FEMUR HEAD REIMPLANTATION

[76] Inventors: Christos Dimakos, Prinzenstr. 11,, 4600 Dortmund 1; Gerhard Radtke, Neue Sendstr. 2b, 4600 Dortmund 12, both of Fed. Rep. of Germany

[21] Appl. No.: 491,972

[22] Filed: May 5, 1983

Related U.S. Application Data

[63] Continuation of Ser. No. 204,196, Nov. 5, 1980, abandoned.

[30] Foreign Application Priority Data

Nov. 6, 1979 [DE] Fed. Rep. of Germany ....... 2944710

[51] Int. Cl.³ ............................................. A61B 17/00
[52] U.S. Cl. ............................ 128/303 R; 128/92 EC; 29/255
[58] Field of Search .............. 128/92 EC, 345, 303 R; 411/57, 54, 44, 71; 145/30.5; 81/463; 29/255

[56] References Cited

U.S. PATENT DOCUMENTS

| | | | |
|---|---|---|---|
| 2,934,984 | 5/1960 | Woodman | 81/463 X |
| 3,529,497 | 9/1970 | Brooks | 81/463 |
| 4,015,505 | 4/1977 | Murray | 411/57 |

FOREIGN PATENT DOCUMENTS

| | | | |
|---|---|---|---|
| 52169 | 2/1912 | Austria . | |
| 1863282 | 9/1962 | Fed. Rep. of Germany . . | |
| 7629320 | 3/1977 | Fed. Rep. of Germany . | |
| 410276 | 10/1966 | Switzerland . | |
| 603143 | 8/1978 | Switzerland . | |
| 1281863 | 7/1972 | United Kingdom | 128/92 E |
| 1413004 | 11/1975 | United Kingdom | 411/71 |
| 648214 | 2/1979 | U.S.S.R. | 128/92 EC |

*Primary Examiner*—Michael H. Thaler
*Attorney, Agent, or Firm*—Toren, McGeady and Stanger

[57] ABSTRACT

An instrument for removal of a hollow bone cement tube from a femur reimplantation having an elongate hollow tube adapted to be inserted into the bone cement tube to be removed with a collet at the insertion end of the hollow tube being radially expanded to engage the bone cement tube on the interior thereof by rotation of a mandrel having the collet threadedly engaged on the insertion end thereof. The hollow tube engages the collet to prevent relative rotation therewith and to allow the mandrel by threaded engagement with the collet to effect radial expansion thereof.

4 Claims, 3 Drawing Figures

INSTRUMENT FOR REMOVAL OF A BONE CEMENT TUBE IN AN ARTIFICIAL FEMUR HEAD REIMPLANTATION

This is a continuation of Ser. No. 204,196, filed Nov. 5, 1980, now abandoned.

The present invention relates generally to osteoplastic instruments and, more particularly, to a device for removing a bone cement tube in a reimplantation of an artificial femur head from a cavity in the femur by utilization of an extractor which is to be fixed on the bone cement tube.

In alloplasts in the hip joint, it is known to affix an extension on an artificial femur head in a cavity of the femur by means of bone cement.

Implants of this type cannot remain indefinitely in the femur since they may become loose, particularly in the boundary layer region between the bone cement and the femur. When such an implant must be replaced, an essentially cylindrical bone cement tube remains in the bone after removal of the implant. In order for reimplantation to be accomplished, the bone cement tube must be completely removed.

Removal of the old bone cement has heretofore been effected by drilling from above or by laying a bypass obliquely from the bottom in order to enable loosening of all bone cement portions and to facilitate complete removal thereof from the cavity in the femur by means of forceps or other mechanical means or by suction.

It is also known to utilize for this purpose an extractor with a plug thread on the head thereof. The extractor is cut far down into the bone cement tube in order to obtain a sufficient hold for ejecting the bone cement tube.

Known instruments of this type involve, among other considerable drawbacks, the risk, particularly in older patients, that the bone wall will splinter since the radial stress produced by the plug thread can be greater than the strength of the bone itself. Furthermore, there is no assurance with a known instrument that all the cement will be detached at the base of the cavity in the bone.

The present invention is directed toward provision of an instrument whereby radial forces on the bone may be completely eliminated, particularly when the cement bone tube is ejected, while at the same time enabling complete removal of the bone cement from the femur.

SUMMARY OF THE INVENTION

Briefly, the present invention may be described as an instrument or extractor for removal of a hollow bone cement tube from a femur which comprises a hollow tube having a control element guided in the interior thereof and a spreader element or collet arranged on the insertion end of the hollow tube concentrically therewith.

More specifically, the control element comprises a mandrel which extends through the interior of the hollow tube and which is freely rotatable therein. The mandrel, at the insertion end thereof, is threadedly engaged with the collet or spreader element and the internal end of the hollow tube is formed to engage the spreader element to prevent relative rotation between the hollow tube and the spreader element. Thus, by manipulation of the mandrel or control element from the operating end of the hollow tube, the collet or spreader element may be drawn outwardly against the hollow tube and thereby spread radially so as to come into engagement with the interior end of the bone cement tube to be removed thereby facilitating removal of the bone cement tube while applying essentially only axial forces thereto.

With the instrument in accordance with the present invention, it is possible to grasp the bone cement tube from the interior thereof with the spreading element after the extractor has been introduced into the cavity and to eject the bone cement tube. For grasping the bone cement tube, it may be necessary in some cases to extend the inner bore slightly in order to obtain sufficient room for the spreading element beneath the bone cement tube. Manipulation is effected as a rule with corresponding optical supervision, for example by an X-ray picture projected on a television screen.

By virtue of a further development of the invention, the hollow tube is provided at one end thereof with a zone having a male thread for engagement thereof in a female thread which is provided in the bone cement tube. This design has the advantage that the hollow tube is able to transmit tensile stresses on the bone cement tube through the male thread without radial stresses, as would otherwise appear with state of the art devices.

In accordance with another feature of the invention, the hollow tube is equipped at its end facing the spreading element with control faces for the spreading element and in an advantageous embodiment of the invention, the control faces are designed as circumferential conical surfaces having an outwardly directed slope. In order to prevent the spreading element from making a full rotation when the element admitting the spreading element is operated, the conical surface can be provided, in accordance with the invention, with friction-increasing grooves, cams, recesses, etc. For example, a friction-increasing coat may be provided at this point.

In a particularly advantageous aspect of the invention, the spreading element is designed as a hollow frustum with a female thread with the larger diameter corresponding substantially to the outside diameter of the hollow tube in the introduction position of the device. This design ensures that the device will require only a small bore for introduction into the operating position since no parts will project in this position which would require a larger opening.

In order to maintain a particularly efficient spreading element, slots are provided in accordance with the invention in the shell of the hollow cone, beginning from the range of the larger diameter in order to produce spreading wings, these slots extending preferably up to the center of the longitudinal extension of the hollow frustum.

As a rule, the spreading element is disposable and is made of a corresponding spreadable material which is, on the one hand, deformable to a certain extent without rupturing and which, on the other hand, is suitable for transmitting the pressures produced during ejection of the bone cement from the device to the underside of the bone cement tube. This design with the slots requires, therefore, a particularly careful manufacture of the spreading wings.

In accordance with a further feature of the invention, the control element is provided with a threaded zone which cooperates in the operating position with a female thread on the spreading element and, in the opposite range, with a shoulder to bear upon the hollow tube. By rotation of the control element, the shoulder bears at first at one end on the hollow tube while at the opposite lower end the spreading element bears on the control faces. By further rotation thereof, the control element will pull the spreading element over the thread in the direction of the upper shoulder and operates to widen it over the control faces. The extent of widening can be observed by a surgeon through a corresponding optical instrument.

In order to hold and operate the elements of the devices, the hollow tube and the control element are each provided with a handle which may be either detachable or integrally formed therewith, depending upon requirements.

In order to introduce a substantially axial, centrally directed striking force, a stop and an axially symmetrical striker are provided in a further advantageous embodiment of the invention upon the hollow tube in the range of the front end thereof when in the operating position, with the striker being displaceable on the hollow tube toward the stop. The axially symmetrical striker guided upon the hollow tube will ensure, in a particularly advantageous manner, that a striking or ejection force may be applied exactly in the direction of the longitudinal axis of the device without canting of the device so that the bone cement tube can be driven out as a whole.

In accordance with the invention, the stop member for the striker and the handle on the hollow tube may also be made as a single piece.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

DETAILED DESCRIPTION OF THE PREFERRED EMBODIMENT

Figure 1:
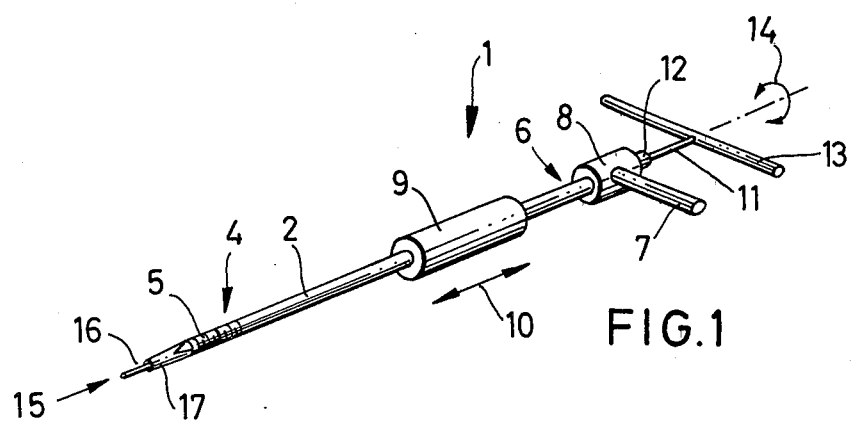
FIG. 1 is a perspective view generally depicting the instrument in accordance with the present invention.

The removal instrument in accordance with the present invention is generally designated with the reference numeral 1 in the drawing and is shown as formed substantially as an elongated extractor whose basic element is a hollow tube 2 having an end 4 which may be inserted into operating position into the interior of a femur 3. The insertion end 4 of the hollow tube 2 is provided with a thread 5 and the opposite or operating end 6 of the device is provided with a stop member 8 having a handle 7 rigidly connected thereto. Arranged on the hollow tube 2 is a hollow cylindrical striker 9 which is displaceable in the axial direction thereof as indicated by the double arrow 10.

On the interior of the extractor or hollow tube 2 there is arranged a control element or mandrel 11 which includes a shoulder 12 adapted to bear against the stop member 8 on the side of the stop member 8 remote from the striker 9. The control element or mandrel 11 is equipped with a handle 13 with which the element 11 may be rotated in two directions as indicated by the double arrow 14.

The insertion end 15 of the control element 11 is provided with a threaded portion 16 upon which a spreading element or collet 17 is arranged, with the spreading element 17 having a female thread 18 adapted to engage with the thread 16 on the control element 11.

Figure 2:
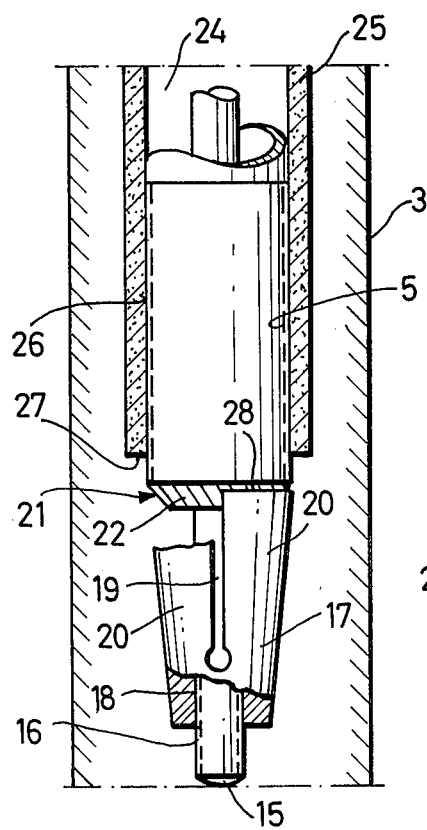
FIG. 2 is a sectional view showing the device on a larger scale during operation thereof at its introductory position.
Figure 3:
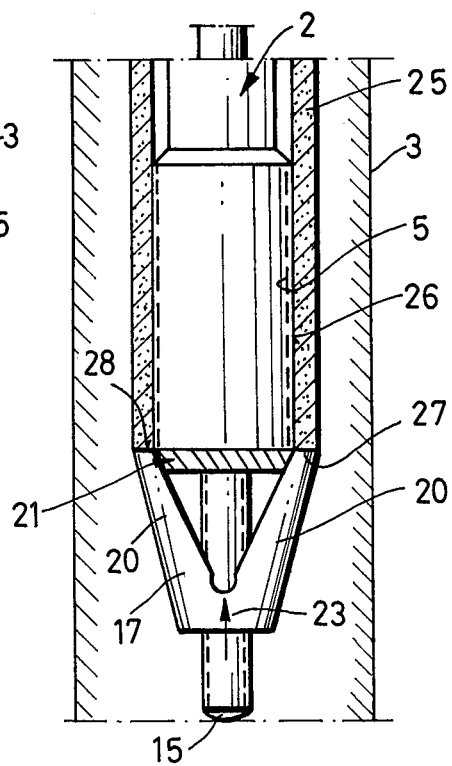
FIG. 3 is a sectional view showing the device after the spreading element has been spread to the ejection position.

The spreading element 17 is formed substantially as a frustum as will be seen particularly from FIGS. 2 and 3, with the larger diameter thereof facing the hollow tube 2 corresponding substantially to the outside diameter of the tube 2 with the device shown in the introductory position represented in FIG. 2. The spreading element or collet 17 is formed with axially extending slots 19 which extend partially along the length thereof and which define therebetween spreading wings 20, with four wings 20 and slots 19 being provided in the spreading element 17 by way of example.

The insertion or bottom free end 4 of the extractor is equipped with control faces 21 which, in the example depicted, are formed as a conical surface having provided thereon friction-increasing webs 22 which during operation will prevent the spreading element 17 from rotating relative to the hollow tube 2 when the mandrel or control element 11 is rotated by manipulation of the handle 13. Thus, the spreading element 17 will be pulled in the direction of the arrow 23 shown in FIG. 3 toward and over the bottom or insertion end 4 of the hollow tube 2 and it will be widened as a result of rotation of the control element 11.

In the operation of the device in accordance with the present invention, after an implant has been removed from a femur 3, a slightly upwardly widening cavity 24 will remain, as best seen in FIG. 2, with this cavity being lined with a bone cement tube 25. The originally closed grooved zone of the bone cement 25 is opened with a drill and subsequently the bottom end of the bone cement tube 25 is provided with a female thread. Due to the conical form of the cavity 24, only the bottom end of the cavity is equipped with a thread with corresponding dimensioning of the thread tap.

The extractor device of the present invention may now be introduced into the bone cement tube 25 and into the blind bore represented thereby and the extractor may be threadedly engaged with the tube 25 by screwing the hollow tube 2 with its thread 5 into the thread 26. The spreading element will be introduced down into the bottom end 27 of the bone cement tube 25 as shown in FIG. 2. By holding the hollow tube 2 with the handle 7 and by rotating the control element of the mandrel 11 by manipulation of the handle 13 in one of the directions of the double arrow 14, the spreading element will be prevented by the webs 22 from rotating. As a result, it will be pulled upwardly in the direction of the arrow 23 over threaded joint 16/18 and it will widen radially so far that the upper edges 28 of the spreading wings 20 will engage the bottom ends 27 of the bone cement tube 25 in the manner shown in FIG. 3. The extent of spreading of the element 17 may be controlled and determined by a surgeon by means of a monitor and X-ray supervision.

Subsequently, the striker 9 may be operated thereby permitting the introduction of a centered force as a result of the concentric arrangement of the apparatus. Because of the sharp blows which will be applied, the bone cement tube 25 will normally be ejected out of the femur 3 in one piece without any residue remaining in the cavity. This result is enhanced by the fact that the opening widens slightly conically taken in the upward or outward direction of the femur 3.

Naturally, the embodiment described above may be modified in various ways without departing from the spirit and scope of the present invention. The invention is not limited to the specific design of the spreading element, the handles or the striker depicted and, in the same manner, it is possible to spread cams pivotally mounted at the bottom end of the extractor which are controlled over the control element. The unthreaded portion of the extractor may also be provided with a smaller diameter, in accordance with the present invention, than the diameter of the threaded front portion, which is particularly expedient when the cavity does not widen toward the outside, but has a constant diameter.

While a specific embodiment of the invention has been shown and described in detail to illustrate the application of the inventive principles, it will be understood that the invention may be embodied otherwise without departing from such principles.

What is claimed is:

1. An instrument for removing a hollow bone cement tube from a cavity in a bone, said bone cement tube having a generally annular tubular configuration with a radially innermost diameter and a radially outermost diameter, said instrument comprising:

a hollow tube having an open operating end and an open insertion end adapted to be placed within said bone cement tube, said hollow tube having a radially outermost diameter which is smaller than said radially innermost diameter of said bone cement tube to enable passage of said hollow tube within and through said bone cement tube;

male thread means in said hollow tube adapted for engagement with female thread means in said bone cement tube for affixing said hollow tube with said bone cement tube;

a mandrel extending through the interior of said hollow tube from said operating end to beyond said insertion end and freely rotatable relative to said hollow tube;

collet means attached to said mandrel at an end thereof extending beyond said insertion end of said hollow tube, said collet means being adapted to normally extend radially no further than the outside diameter of said hollow tube during insertion of said hollow tube into said bone cement tube;

said collet means being formed with a frustoconical configuration having a larger diameter portion adjacent said insertion end of said hollow tube which in the insertion position of said collet means extends no further than the outer diameter of said hollow tube;

longitudinal slots formed in said collet means for enabling said collet means to be radially spread to have said larger diameter portion extend radially beyond beyond the outer diameter of said hollow tube;

internal thread means in said collet means and external thread means on said mandrel for engagement with said internal thread means;

tapered peripheral surface means formed on said larger diameter portion of said collet means adapted to engage complementary tapered peripheral surface means formed on said insertion end of said hollow tube to facilitate spreading action of said collet means when said collet means is urged against said insertion end by operation of said mandrel through interengagement of said external thread means and said internal thread means;

said mandrel being operable to urge said collet means against said insertion end of said hollow tube to radially spread said collet means beyond the outer diameter of said hollow tube in order that said collet means may be brought into abutment with the inner end of said hollow bone cement tube to facilitate removal thereof by manipulation of said mandrel after said collet means has been inserted together with said hollow tube through said bone cement tube to be located on an inner end thereof; and means for applying to the inner end of said bone cement tube through the engagement of said spread collet means with said bone cement tube an outwardly directed force for facilitating removal of said bone cement tube.

2. An instrument according to claim 1 wherein said longitudinal slots in said collet means extend substantially to the middle of the longitudinal dimension thereof.

3. An instrument according to claim 1 wherein said complementary peripheral surface means on said hollow tube is provided with an irregular configuration to enhance frictional surface contact thereof with said tapered peripheral surface means on said collet means.

4. An instrument according to claim 1 wherein said means for applying an outwardly directed force comprise striker means slidably mounted on the outside of said hollow tube and adapted to apply an impact force to said hollow tube, said mandrel having a shoulder adapted to bear against the operating end of said hollow tube in order that an impact force applied to said hollow tube by said striker means will be transferred from said hollow tube to said mandrel and to said collet means for urging said bone cement tube out of said bone.

* * * * *